United States Patent [19]

Keys, Jr.

[11] Patent Number: 4,543,950

[45] Date of Patent: Oct. 1, 1985

[54] PATIENT'S MOUTHPIECE

[76] Inventor: Richard H. Keys, Jr., 170 Magnolia Ave., Cincinnati, Ohio 45246

[21] Appl. No.: 599,003

[22] Filed: Apr. 11, 1984

[51] Int. Cl.$^4$ .............................................. A61M 29/00
[52] U.S. Cl. ........................ 128/136; 128/203.29; 128/206.29; 128/341; 128/12; 128/205.25
[58] Field of Search ............ 128/136, 207.14, 207.15, 128/359, 341, 346, 12, 206.12–206.29, 205.25; 2/2; 433/138, 140, 6; 119/29, 29.5, 129; 604/290

[56] References Cited

U.S. PATENT DOCUMENTS

| | | |
|---|---|---|
| D. 246,671 | 12/1977 | Cerniway . |
| 316,636 | 4/1885 | Miles ................... 128/207.14 |
| 903,344 | 11/1908 | Wackler . |
| 1,483,694 | 2/1924 | Stukey ........................ 128/136 |
| 2,274,814 | 3/1942 | West . |
| 2,625,155 | 1/1953 | Engelder . |
| 2,857,909 | 10/1938 | Johnson ....................... 128/136 |
| 2,867,212 | 1/1959 | Nunn, Jr. ..................... 128/136 |
| 2,877,764 | 3/1959 | Galleher, Jr. . |
| 2,917,045 | 12/1959 | Schildknecht et al. . |
| 3,052,887 | 9/1962 | Sockel et al. . |
| 3,089,485 | 5/1963 | Hirschhorn ................... 128/136 |
| 3,106,916 | 10/1963 | Matthes ..................... 128/202.28 |
| 3,126,002 | 3/1964 | Owens ........................ 128/136 |
| 3,139,088 | 6/1964 | Galleher, Jr. ................ 128/136 |
| 3,303,845 | 2/1967 | Detmer, III ................ 128/202.28 |
| 4,053,984 | 10/1977 | Moss ............................ 128/12 |
| 4,090,511 | 5/1978 | Gray ......................... 128/207.14 |
| 4,222,378 | 9/1980 | Mahoney ..................... 128/207.14 |
| 4,270,531 | 6/1981 | Blachly et al. ................ 128/136 |
| 4,305,387 | 12/1981 | Reist-Kundig et al. ....... 128/207.14 |
| 4,305,709 | 12/1981 | Bruhn et al. ................. 433/136 |
| 4,459,105 | 7/1984 | Klein ............................ 433/6 |
| 4,470,413 | 9/1984 | Warncke ..................... 128/206.24 |

*Primary Examiner*—Henry J. Recla
*Assistant Examiner*—Karin M. Reichle
*Attorney, Agent, or Firm*—Wood, Herron & Evans

[57] ABSTRACT

A toroid shaped mouthpiece that is inserted into a patient's mouth between the patient's gums and cheeks. The mouthpiece is particularly configured to sustain an oral space through which the patient can breathe from an anesthesia face mask. With the anesthesia face mask in place over the patient's nose and mouth cavities, the mask generates a good seal with the patient's cheeks because the mouthpiece insures that the cheeks will remain flushed out against the mask. This is particularly advantageous in the case of edentulous patients.

7 Claims, 5 Drawing Figures

PATIENT'S MOUTHPIECE

This invention relates to mouthpieces. More particularly, this invention relates to a patient's mouthpiece particularly adapted for use during the anesthetization of patients.

It is necessary to anesthetize patients, i.e., to put patients to sleep, in connection with many surgical techniques. In the case of a general anesthesia of the gaseous type, the anesthesiologist causes the patient to breathe an air/anesthetic mixture through use of a face mask. The face mask is sized and configured to cover the patient's mouth and nose cavities so that the patient can breathe only what the anesthesiologist wishes the patient to breathe.

The anesthesiologist faces a practical problem with the edentulous patient. When it is attempted to put an edentulous patient to sleep with general gaseous type anesthesia through use of a face mask, the face mask may tend to lose its continuity of seal with the patient's cheeks. This is due to the fact that, with the patient's teeth missing, there is no structure interiorly of the patient's mouth to hold the cheeks against the face mask. If such a concavity occurs in one or both of the patient's cheeks as the patient breathes through the mask, the anesthesiologist tends to lose control over the correct anesthesia/air mixture which the patient breathes. In practice, the current way of solving this problem is to put a rag or towel or sponge or the like between the cheek's outer surface and the face mask's periphery in order to maintain the desirable cheek/face mask seal with the sleeping or anesthetized patient. This kind of a make shift approach is necessary in order to insure that the patient's breathing will occur solely with that gaseous mixture provided through the face mask.

Accordingly, it has been the objective of this invention to provide a mouthpiece for a patient that is particularly useful with an anesthesia face mask, as well as a method of anesthetizing a patient through use of that mouthpiece, where the mouthpiece insures a reasonable seal between, i.e., continuity with, the patient's cheeks and the face mask even if the patient is edentulous. In accord with this objective, and in preferred form, the patient's mouthpiece of this invention is in the form of a generally elliptical toroid as viewed from the front of the patient's face. The toroid is also of an inwardly curved concave configuration when viewed from the side of patient's face and from above the patient's head. The toroid is also of an outwardly curved convex configuration when viewed from in front of the patient's face. This results in a mouthpiece with upper and low jaw sections connected by hinge sections. In preferred form each of the hinge sections is of a cross-sectional area substantially greater than the cross-sectional area of the jaw sections. And in preferred form, the mouthpiece is formed from a generally flexible material that permits the mouthpiece's as-molded, in use configuration to be somewhat altered within the patient's mouth, when desired by the anesthesiologist, and depending on the size characteristics of the patient's mouth, while retaining the general structural integrity of the unit in order to establish a desired seal between the patient's cheeks and the face mask during use of the face mask.

Other objectives and advantages of this invention will be more apparent from the following detailed description taking in connection with the drawings in which.

Figure 2:
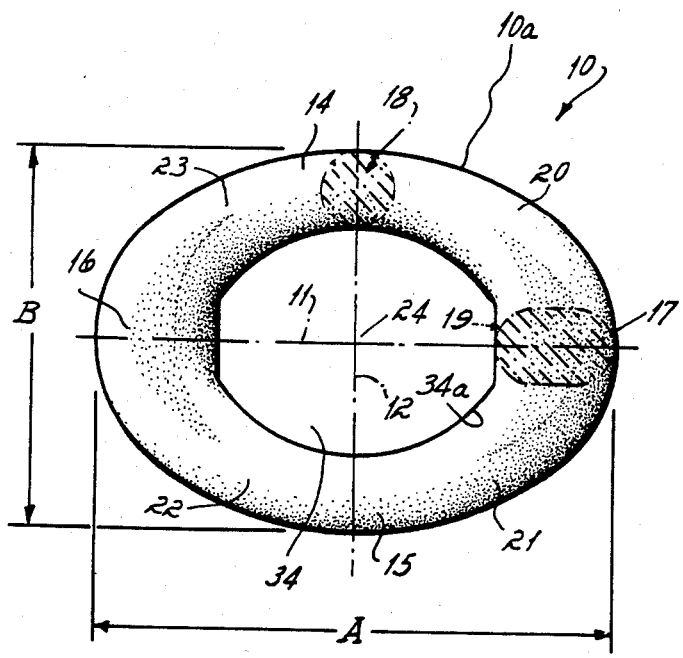
FIG. 2 is a front view of the patient's mouthpiece in a flattened or uncurved state.

The patient's mouthpiece 10 in accord with the principles of this invention, in its flattened or uncurved state as shown in FIG. 2, is in the form of a toroid. The toroid 10, which preferably is an elliptically-shaped ring having an oral port 34 when viewed from the front in its flattened state (as seen in FIG. 2), includes a major or x axis 11 and a minor or y axis 12. The width A of the toroid 10 along its major axis 11 is preferably about 1.4 times the width B of the toroid along its minor axis 12, although for the human mouth this width ratio may range between about 1.1 and about 1.7.

The elliptical toroid 10 includes an upper jaw section generally indicated at 14, a lower jaw section generally indicated at 15, and opposed hinge or side sections generally indicated at 16, 17 which connect the upper and lower jaw sections. The toroid's cross-sectional configuration is illustrated in phantom for the jaw sections 14, 15 and the hinge sections 16, 17, by shaded areas 18, 19, respectively, in FIG. 2. Note the cross-sectional configuration 18 of each jaw section 14, 15 along the minor axis 12 of the elliptical toroid 10 is generally circular in configuration. And note the cross-sectional configuration 19 of each hinge section 16, 17 along the major axis 11 of the elliptical toroid 10 is generally elliptical in configuration. Preferably the cross-sectional area 19 of each hinge section 16, 17 of the elliptical toroid 10 along its major axis 11 is about 1.5 times as great as the cross-sectional area 18 of each jaw section 14, 15 of the elliptical toroid along its minor axis 12. When sized for use in the human mouth, each hinge section's cross-sectional area 19 should be between about 1.2 and about 1.8 times the size of a jaw section's cross-sectional area 18. The fact that the cross-sectional geometry, and the cross-sectional area, of the mouthpiece's jaw sections 14, 15 along the minor axis 12 vis-a-vis the mouthpiece's hinge sections 16, 17 along the major axis 11 are different one from the other results in transition sections 20–23 that interconnect the jaw sections with the hinge sections. The transition sections 20–23 vary in radial (relative to the toroid's center point 24) cross-sectional configuration and geometry between each transition section's associated hinge section 16 or 17 and jaw section 14 or 15. The larger cross-sectional area and the different cross-sectional geometry of the toroid's hinge sections 16, 17 vis-a-vis the toroid's jaw sections 14, 15 is important relative to this invention. The importance lies in the fact that when the mouthpiece 10 is used with edentulous patients, and since it is very important that an anesthesia face mask 30 maintain contact with a patient's cheeks 31, the greater bulk 16, 17 of the mouthpiece is provided in that area which underlies the patient's cheeks.

Figure 3:
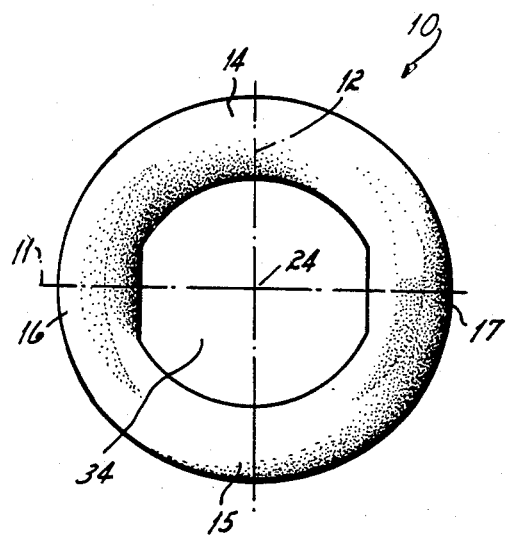
FIG. 3 is a front view of the patient's mouthpiece in the curved or use state.
Figure 4:
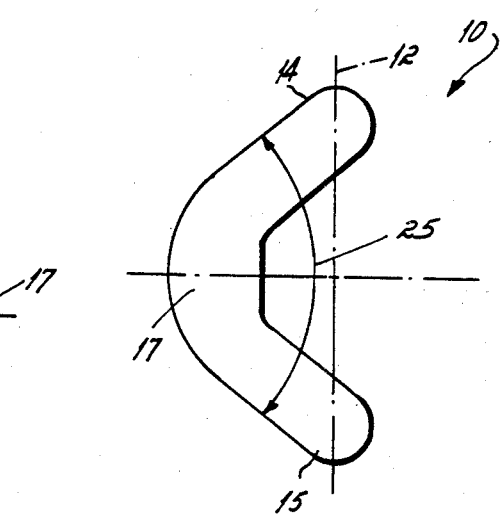
FIG. 4 is a side view of the patient's mouthpiece as shown in FIG. 3.
Figure 5:
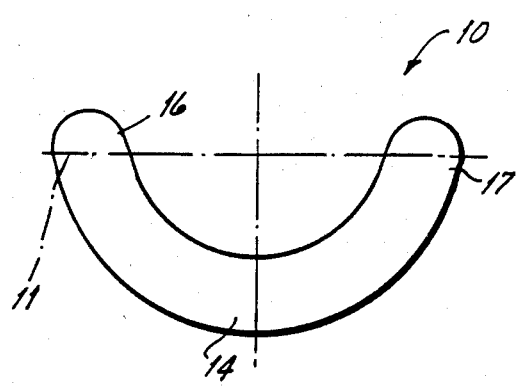
FIG. 5 is a top view of the patient's mouthpiece as shown in FIGS. 3 and 4.

The configuration of the elliptical toroid 10 in the patient use position is illustrated in FIGS. 3–5. When viewed from the side of a patient's face 32 as installed within the patient's mouth 33, and as shown in FIG. 4, the elliptical toroid is provided with a generally concave arcuate configuration, the elliptical toroid being curved relative to its major x-axis 11. This lateral curvature of the mouthpiece 10 is preferably such that the mouthpiece's upper 14 and lower 15 jaw sections are angled relative one to the other at an included angle 25 of about 80°, but that included angle 25 may be within a range of between about 40° and about 120°. The importance of this side or concave curvature aspect of the mouthpiece 10 is to insure that the mouthpiece's jaw sections 14, 15 cooperate with its hinge sections 16, 17 to maintain an oral port or space 34 therebetween when it is installed in the patient's mouth 33. Preferably, and when viewed as shown in FIG. 2, the area defined by periphery 34a of the oral space or port should be between about 25% and about 50% of the area defined by the periphery 10a of the mouthpiece. This oral space or port 34 defined by the mouthpiece 10 is very important as it permits an attending physician to breathe the patient through a face mask 30 since it insures that the patient's oral cavity or mouth 33 remains open to the gaseous anesthesia. The mouthpiece 10 is also curved in a generally concave configuration when viewed as shown in FIG. 5, that curvature being relative to the mouthpiece's minor or y-axis 12. The generally arcuate configuration established in this top view is such as to permit the mouthpiece's upper 14 and lower 15 jaw sections to conform or generally lie against the patient's upper and lower gums when it is installed within the patient's mouth 33. Accordingly, the mouthpiece 10 is provided with a generally concave curvature relative to its X-axis 11, and a generally concave curvature relative to its Y-axis 12, and a generally convex curvature when installed in a patient and as viewed from in front of the patient's face 32.

The patient's mouthpiece 10 of this invention is preferably formed from a material that is flexible or bendable. In this regard, it is preferred that the material have a hardness of between about 50 and about 60 Durometer. One preferred material useful in molding the mouthpiece of this invention is a surgical silicone rubber. When a mouthpiece 10 in accord with this invention is fabricated from material having the hardness characteristics listed above, a generally standard size mouthpiece can be easily flexed to conform to a patient's jaws interiorly of the patient's mouth 32 by the attending physician. This is important, particularly in the case of edentulous patients, because it permits the mouthpiece 10 to be configured or tailored to the particular patient with which the physician is concerned while insuring that the anesthesia face mask 30 will maintain the desired seal against the outer surface of the patient's face 32 in the area of the patient's cheeks 31 when the anesthesia is administered. Further, this hardness characteristic of the mouthpiece 10 is useful vis-a-vis the face mask 30 in that by pressing the face mask itself onto the patient's face 32 the periphery 35 of that face mask also tends to cause the mouthpiece interiorly of the patient's mouth to flex so as to provide a desirable seal between the face mask and the patient's face.

Figure 1:
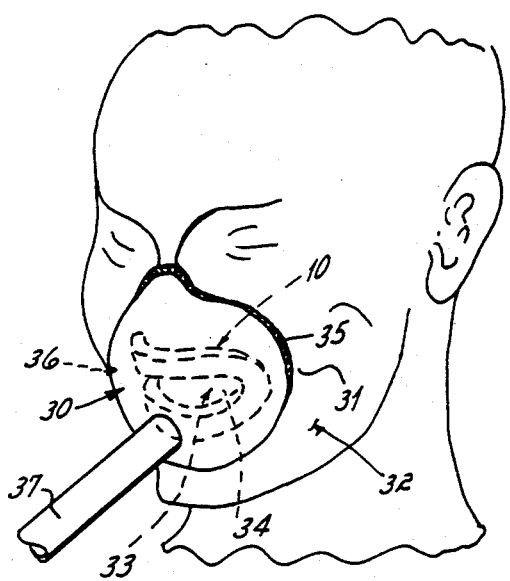
FIG. 1 is a perspective view illustrating the general use of an anesthesia face mask with an edentulous patient where the mouthpiece of this invention is installed in the patient's mouth.

In use, the mouthpiece 10 as shown in FIGS. 3–5 is installed in a patient's mouth 33 as shown in FIG. 1. In the case of an edentulous patient, the mouthpiece 10 is placed in the mouth 33 in such a way as to push the cheek areas 31 generally outwardly. Since the upper 14 and lower 15 jaw sections of the mouthpiece are thinner than the hinge sections 16, 17 of the mouthpiece, those hinge sections provide a greater space filler behind the patient's cheek areas 31 as opposed to a lesser space filler behind the patient's lips 36. And with the mouthpiece 10 installed between the patient's jaws and face, and because of its hardness and flexibility characteristics, it is thereafter conformed to the interior of the patient's mouth as desired by the attending physician. Since the mouthpiece 10 is sized generally to cooperate with the periphery of an aesthesia face mask 30, and with the mouthpiece properly installed, the face mask is placed over the patient's mouth and nose cavities. The face mask 30 maintains a good seal with the patient's cheek areas 31 because the mouthpiece insures that the cheeks will remain flushed out against the face mask. And further, conformation of the mouthpiece 10 to the face mask's periphery 35 can occur during use of the face mask because the of the flexibility characteristics of the mouthpiece. Thereafter, the anesthesia mask's periphery 35 is placed on a patient's cheek areas 31 in juxtaposition at least to the hinge sections 16, 17 of the mouthpiece located inside the patient's mouth. And thereafter the patient is caused to breathe a gaseous anesthesia mixture through that face mask 30 as fed to the face mask by hose 37. A reasonable seal is maintained between the face mask's periphery 35 and the outer surface of the patient's face 32, particularly in cheek areas 31, even for those patients that are edentulous, while the patient breathes through the face mask.

Having described in detail the preferred embodiment of my invention, what I desire to claim and protect by Letters Patent is:

1. A mouthpiece for a patient to aid in maintaining a seal between a face mask and cheeks of a patient upon exposing that patient to a gaseous anesthesia through use of said face mask, said mouthpiece comprising:

a substantially normally curved, flexible one-piece member being generally elliptically-shaped when flexed into a generally flat configuration and sized to be received in a patient's mouth between the patient's jaw, lips and cheeks and underlie the patient's lips and cheeks, said member having a centrally elliptically-shaped oral port and having upper and lower jaw sections connected one with the other by side sections, said member having a major axis which intersects said mouthpiece's side sections and a minor axis which intersects said mouthpiece's jaw sections when said unit is in said flattened state, said jaw and side sections having cross-sectional areas as measured along said minor and major axis, respectively, said jaw sections' cross-sectional areas being substantially circular from which that cross-sectional area diverges to a substantially larger, thicker elliptical cross-sectional area at said side sections, said jaw sections' cross-sectional areas being adapted to be situated entirely between the gums and the lips and cheeks of the patient and said side sections being adapted to be situated between the patient's gums and cheeks, and said member having sufficient thickness and having sufficient hardness such that, when inserted in the patient's mouth, the patient's lips are held in spaced-apart relationship to facilitate the flow of gas into and out of the patient's mouth and the patient's cheeks are urged outwardly to cooperate with the periphery of an anesthesia face mask in order to maintain a seal between the face mask and the patient's cheek areas as desired by the attenting physician during breathing of that patient through the face mask.

2. A mouthpiece as set forth in claim 1, said mouthpiece being fabricated from a flexible material having a hardness of between about 50 and about 60 Durometer, and said oral port being between about 25% and about 50% of the area defined by the periphery of said member when said member is flexed into said generally flat configuration with no curvature relative to its major and minor axis.

3. A mouthpiece as set forth in claim 2, said side sections having a cross sectional area between about 1.2 and about 1.8 times the cross sectional area of said jaw sections.

4. A mouthpiece as set forth in claim 3, said mouthpiece being curved relative to its major axis in a generally arcuate configuration to define an included angle between said jaw sections when said unit is in said curved state.

5. A mouthpiece as set forth in claim 4, said mouthpiece being curved relative to its minor axis in a generally arcuate configuration to define an included angle between said side sections when said member is in said normally curved state.

6. A mouthpiece as set forth in claim 5, said included angle between said jaw sections being between about 40° and about 120°.

7. A method of anesthetizing a patient through use of a gaseous anesthesia, said method comprising the steps of (a) providing a mouthpiece for the patient to aid in maintaining a seal between a face mask and the cheeks of a patient upon that patient being exposed to gaseous anesthesia through the use of said face mask, said mouthpiece comprising:

a substantially normally curved flexible one-piece member being generally elliptically-shaped when flexed into a generally flat configuration and sized to be received in a patient's mouth between the patient's jaw, lips and cheeks and underlie the patient's lips and cheeks, said member having a centrally elliptically-shaped oral port and having upper and lower jaw sections connected one with the other by side sections, said member having a major axis which intersects said mouthpiece's side sections and a minor axis which intersects said mouthpiece's jaw sections when said unit is in said flattened state, said jaw and side sections having cross-sectional areas as measured along said minor and major axis, respectively, said jaw sections' cross-sectional areas being substantially circular from which that cross-sectional area diverges to a substantially larger, thicker elliptical cross-sectional area at said side sections, said jaw sections' cross-sectional areas being adapted to be situated entirely between the gums and the lips and cheeks of the patient and said side sections being adapted to be situated between the patient's gums and cheeks, said member having sufficient thickness and having sufficient hardness such that, when inserted within a patient's mouth, the patient's lips are held in spaced-apart relationship to facilitate the flow of gas into and out of the patient's mouth and the patient's cheeks are urged outwardly to cooperate with the periphery of an anesthesia face mask in order to maintain a seal between the face mask and the patient's cheek areas as desired by the attending physician during breathing of that patient through the face mask, (b) inserting said mouthpiece into the patient's mouth so said mouthpiece's entire jaw sections are between the patient's lips and gums and cheeks such that the lips are held in spaced-apart relationship and said mouthpiece's side sections are between the patient's gums and cheeks such that said cheeks are urged away from said gums, (c) thereafter placing a face mask on the exterior of the patient's face so that said mask's periphery on the patient's cheeks is juxtaposed at least to the side sections of said mouthpiece located in said patient's mouth, and (d) thereafter selectively providing gaseous anesthesia to said face mask.

* * * * *